(12) United States Patent
Hamano

(10) Patent No.: US 9,372,215 B2
(45) Date of Patent: Jun. 21, 2016

(54) ELECTRICAL RESISTANCE MEASUREMENT APPARATUS AND ELECTRICAL RESISTANCE MEASUREMENT METHOD

(71) Applicant: FURUKAWA CO., LTD., Tokyo (JP)

(72) Inventor: Akihide Hamano, Tsukuba (JP)

(73) Assignee: FURUKAWA CO., LTD., Tokyo (JP)

( * ) Notice: Subject to any disclaimer, the term of this patent is extended or adjusted under 35 U.S.C. 154(b) by 56 days.

(21) Appl. No.: 13/786,825

(22) Filed: Mar. 6, 2013

(65) Prior Publication Data

US 2013/0249573 A1 Sep. 26, 2013

(30) Foreign Application Priority Data

Mar. 21, 2012 (JP) ................................. 2012-063851

(51) Int. Cl.
*G01R 27/02* (2006.01)
*G01N 21/3581* (2014.01)

(52) U.S. Cl.
CPC ............ *G01R 27/02* (2013.01); *G01N 21/3581* (2013.01)

(58) Field of Classification Search
CPC .......... G01N 21/3581; G01N 21/3563; G01N 21/9505; G01N 21/3568; G01N 21/3586; G01N 21/359; G01N 21/3595; G01R 27/02
USPC ................................. 324/691, 702, 722, 791, 324/754.21–754.23; 356/51
See application file for complete search history.

(56) References Cited

U.S. PATENT DOCUMENTS

| 2001/0029436 | A1  | 10/2001 | Fukasawa |
| 2003/0164946 | A1* | 9/2003  | Borden et al. ................. 356/432 |
| 2004/0119978 | A1* | 6/2004  | Borden et al. ................. 356/432 |
| 2009/0039878 | A1* | 2/2009  | Oya et al. ....................... 324/222 |

(Continued)

FOREIGN PATENT DOCUMENTS

| EP | 2233914    | 9/2010 |
| JP | 09-054125  | 2/1997 |
| JP | 10-253674  | 9/1998 |

(Continued)

OTHER PUBLICATIONS

Ching-Wei Chen et al., "Frequency-Dependent Complex Conductivities and Dielectric Responses of Indium Tin Oxide Thin Films from the Visible to the Far-Infrared", Dec. 12, 2010, IEEE Journal of Quantum Electronics, vol. 46, No. 12, pp. 1746-1754.*

(Continued)

*Primary Examiner* — Arleen M Vazquez
*Assistant Examiner* — Lee Rodak
(74) *Attorney, Agent, or Firm* — Rankin, Hill & Clark LLP

(57) ABSTRACT

An electrical resistance measurement apparatus includes a light irradiation unit that irradiates a conductive thin film with terahertz light, a reflection light detection unit that detects reflection light from the conductive thin film, and a computer containing a storage that stores correlation between the reflectance of the terahertz light from the conductive thin film and electrical resistance of the conductive thin film. The computer further containing a processor that determines, reflectance of the terahertz light from the conductive thin film based on a result of detection performed by the reflection light detection unit, and determines the electrical resistance of the conductive thin film based on the correlation and a result of the determination of the reflectance.

8 Claims, 2 Drawing Sheets

(56) References Cited

U.S. PATENT DOCUMENTS

| | | | |
|---|---|---|---|
| 2010/0091266 A1* | 4/2010 | Yasuda et al. | 356/51 |
| 2011/0058155 A1* | 3/2011 | Ohno et al. | 356/51 |

FOREIGN PATENT DOCUMENTS

| | | |
|---|---|---|
| JP | 2007-225418 | 9/2007 |
| JP | 2008-032618 | 2/2008 |
| JP | 2009-287960 | 12/2009 |
| JP | 2011-053529 | 3/2011 |

OTHER PUBLICATIONS

P. G. Quincey et al., "Far Infrared Complex Conductivity Measurements on YBaCuO Thin Films", Aug. 30, 1990, Soild State Communications, vol. 76, No. 11, pp. 1281-1284.*

Z.L Pei et al,"Optical and electricla properties of direct-current magnetron sputtered ZnO:Al films," J. Appl. Phys. v90, p. 3432 (2001).*

K. E. Kornelsen, "Far Infrared optical absorption and reflectivity of a superconducting NbN film," Physical Review B, v44, p. 882 (1999).*

Brewer et al., "Optical Properties of Indium Tin Oxide and Fluorine-doped Tin Oxide Surfaces: Correlation of Reflectivity, Skin Depth, and Plasmon Frequency," Journal of Alloys and Compounds v 228, p. 73-79, 2002.*

P. G. Quincey et al. "Far Infrared Complex Conductivity Measurement on YBaCuO Thin Films" Solid State Communications, vol. 76, No. 11, pp. 1281-1284, 1990.

Ching-Wei Chen et al. "Frequency-Dependent Complex Conductivities and Dielectric Responses of Indium Tin Oxide Thin Films from the Visible to the Far-Infrared" IEEE Journal of Quantum Electronics. vol. 46, No. 12, pp. 1746-1754, Dec. 2010.

Extended European Search Report dated Jul. 18, 2013 filed in the corresponding patent application No. 13001394.9.

Hiromasa Ito et al. "Random Frequency Accessible Broad Tunable Terahertz-Wave Source Using Phase-Matched 4-Dimethylamino-N-methyl-4-stilbazolium Tosylate Crystal." Japanese Journal of Applied Physics. vol. 46, No. 11, 2007, pp. 7321-7324.

Japanese Office Action dated Dec. 1, 2015 issued in the corresponding Japanese patent application No. 2012-063851.

* cited by examiner

ELECTRICAL RESISTANCE MEASUREMENT APPARATUS AND ELECTRICAL RESISTANCE MEASUREMENT METHOD This application is based on Japanese patent application No. 2012-063851, the content of which is incorporated hereinto by reference.

BACKGROUND

1. Technical Field

The invention relates to an electrical resistance measurement apparatus and an electrical resistance measurement method.

2. Related Art

As a method of measuring electrical resistance, a method of using a four-terminal method or methods disclosed in Patent Documents 1 and 2 have been proposed.

In the measurement method disclosed in Document 1, Japanese Laid-Open Patent Publication No. 10-253674, a surface which does not have a conductive property is formed on one surface of a conductive thin film, and an electrode comes into contact with the surface which does not have the conductive property, and thus the electrical resistance of a conductive portion is measured.

In the measurement method disclosed in Document 2, Japanese Laid-Open Patent Publication No. H9-54125, a conductive roller is prepared on a conductive thin film, and the electrical resistance of the conductive thin film is measured in a line contact manner.

SUMMARY

However, all of the above-described measurement methods are performed in a contact manner, and there is a possibility of damaging a conductive thin film.

The invention has been made in consideration of the above problems, and an object of the invention is to provide an electrical resistance measurement apparatus and an electrical resistance measurement method which enable the electrical resistance of the conductive thin film to be measured in a contactless manner.

In one embodiment, there is provided an electrical resistance measurement apparatus including: a light irradiation unit that irradiates a conductive thin film with terahertz light; a reflection light detection unit that detects reflection light from the conductive thin film; and a computer containing a storage that stores correlation between the reflectance of the terahertz light from the conductive thin film and electrical resistance of the conductive thin film, the computer further containing a processor that determines reflectance of the terahertz light from the conductive thin film based on a result of detection performed by the reflection light detection unit, and determines the electrical resistance of the conductive thin film based on the correlation and a result of the determination of the reflectance.

According to the electrical resistance measurement apparatus, the correlation between the reflectance of terahertz light from the conductive thin film and the electrical resistance of the conductive thin film is stored in the storage in advance. Further, the reflectance of terahertz light from the conductive thin film is determined, and the electrical resistance of the conductive thin film may be determined based on the result of the determination and the correlation. Therefore, the electrical resistance of the conductive thin film may be measured (determined) in a contactless manner.

In addition, on another embodiment, there is provided an electrical resistance measurement method including: irradiating a conductive thin film with terahertz light; detecting reflection light from the conductive thin film; determining reflectance of the terahertz light from the conductive thin film based on a result of detection performed in said step of detecting the reflection light; and determining the electrical resistance of the conductive thin film based on a result of said step of determining the reflectance and correlation between the reflectance of the terahertz light from the conductive thin film and the electrical resistance of the conductive thin film.

According to the invention, the electrical resistance of a conductive thin film may be measured in a contactless manner.

BRIEF DESCRIPTION OF THE DRAWINGS

The above and other objects, advantages and features of the present invention will be more apparent from the following description of a certain preferred embodiment taken in conjunction with the accompanying drawings, in which.

DETAILED DESCRIPTION

Figure 1:
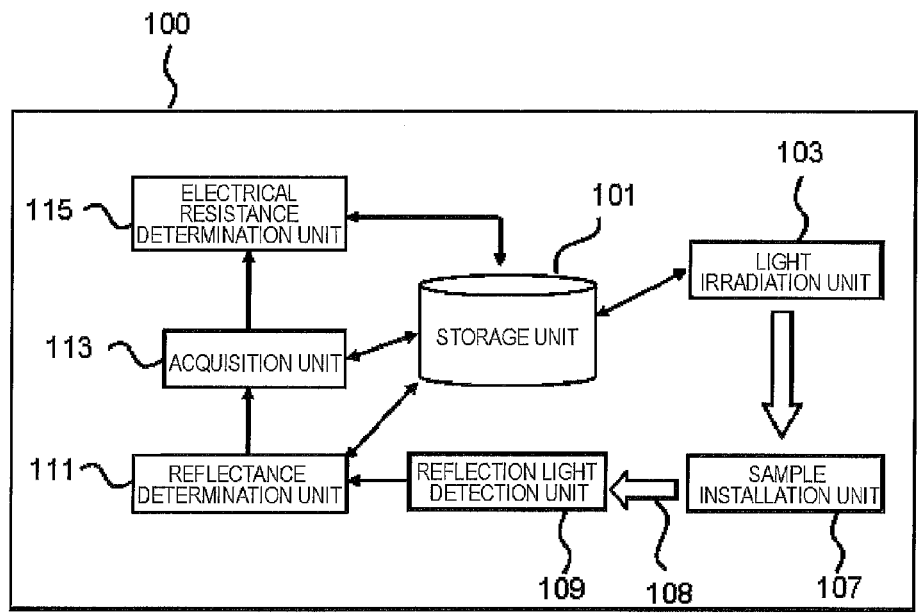
FIG. 1 is a block diagram illustrating an electrical resistance measurement apparatus according to an embodiment.

The invention will be now described herein with reference to an illustrative embodiment. Those skilled in the art will recognize that many alternative embodiments can be accomplished using the teachings of the present invention and that the invention is not limited to the embodiment illustrated for explanatory purposes.

Hereinafter, an embodiment of the invention will be described with reference to the accompanying drawings. Meanwhile, the same reference numerals are used for the same components through all the drawings, and the description thereof will not be repeated.

First Embodiment

Figure 2:
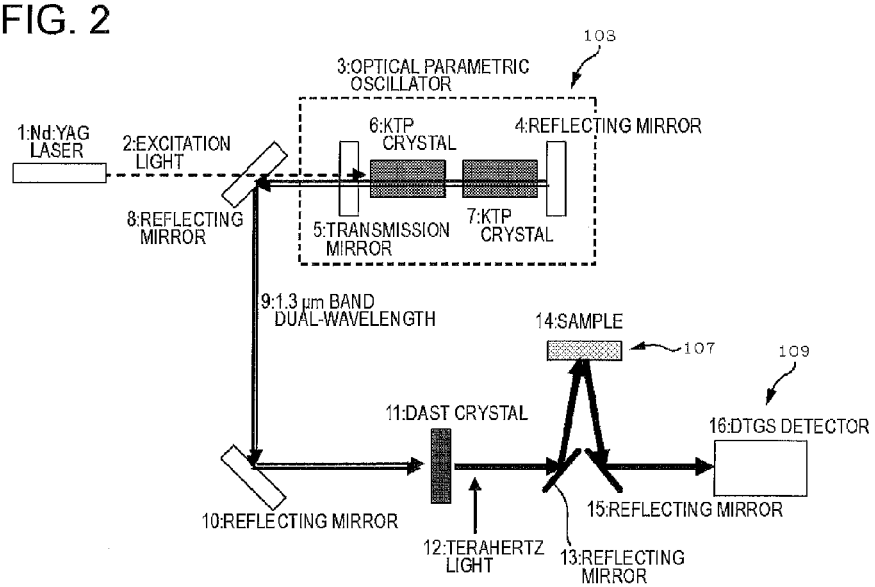
FIG. 2 is a schematic diagram illustrating the configuration of the electrical resistance measurement apparatus according to the embodiment.

FIG. 1 is a block diagram illustrating an electrical resistance measurement apparatus 100 according to an embodiment. FIG. 2 is a schematic diagram illustrating the configuration of the electrical resistance measurement apparatus 100 according to the embodiment.

An electrical resistance measurement apparatus 100 according to the embodiment includes a light irradiation unit 103 that irradiates a conductive thin film with terahertz light, a reflection light detection unit 109 that detects reflection light from the conductive thin film, and a computer containing a storage 101 that stores correlation between the reflectance of the terahertz light from the conductive thin film and electrical resistance of the conductive thin film. The computer further containing a processor (an electrical resistance determination unit 115, an acquisition unit 113 and a reflectance determination unit 111) that determines reflectance of the terahertz light from the conductive thin film based on a result of detection performed by the reflection light detection unit 109, and determines the electrical resistance of the conductive thin film based on the correlation and a result of the determination of the reflectance.

As shown in FIG. 1, the electrical resistance measurement apparatus 100 according to the embodiment includes the light irradiation unit 103, the reflection light detection unit 109, the reflectance determination unit 111, the storage 101, and the electrical resistance determination unit 115. The light irradiation unit 103 irradiates the conductive thin film with terahertz light. The reflection light detection unit 109 detects reflection light 108 from the conductive thin film. The reflectance determination unit 111 determines the reflectance of terahertz light from the conductive thin film based on the result of the detection performed by the reflection light detection unit 109. The storage 101 stores the correlation between the reflectance of terahertz light from the conductive thin film and the electrical resistance of the conductive thin film. The electrical resistance determination unit 115 determines the electrical resistance of the conductive thin film based on the result of the determination performed by the reflectance determination unit 111 and the correlation stored in the storage 101.

In addition, an electrical resistance measurement method according to the embodiment includes the following steps:

1) Process to irradiate the conductive thin film with terahertz light

2) Process to detect the reflection light 108 from the conductive thin film

3) Process to determine the reflectance of terahertz light from the conductive thin film based on a result of the process to detect the reflection light 108

4) Process to determine the electrical resistance of the conductive thin film based on a result of determination in the process to determine reflectance and the correlation between the reflectance of terahertz light from the conductive thin film and the electrical resistance of the conductive thin film The electrical resistance measurement apparatus 100 further includes a sample installation unit 107 in which a sample is installed, and an acquisition unit 113 that acquires information indicative of the correlation from the storage 101. The electrical resistance determination unit 115 determines the electrical resistance of the conductive thin film based on a result of the determination performed by the reflectance determination unit 111 and information indicative of the correlation acquired by the acquisition unit 113.

As shown in FIG. 2, the light irradiation unit 103 includes, for example, an optical parametric oscillator 3.

As excitation light 2 of the optical parametric oscillator 3, the second harmonic (wavelength: 532 nm) of an Nd: YAG laser 1 is used. The excitation light 2 is incident on the optical parametric oscillator 3. The optical parametric oscillator 3 includes a resonator which is configured with a reflecting mirror 4 and a transmission mirror 5, and two KTP crystals (KTiOPO$_4$ crystals) 6 and 7 which are installed in the resonator. The crystal angles of the two KTP crystals 6 and 7 are different from each other a little. It is possible to oscillate dual-wavelengths 9 at a band of 1.3 μm, which are different from each other from the KTP crystal 6 and the KTP crystal 7.

The dual-wavelengths 9 at a band of 1.3 μm are sequentially reflected in a reflecting mirror 8 and a reflecting mirror 10, and incident on a DAST crystal (4-dimethylamino-N-methyl-4-stilabazolium-tosylate) 11. Then, it is possible to extract terahertz light 12 which is equal to or greater than 1.5 THz and equal to or lower than 47 THz due to non-linear optical effect.

The generated terahertz light 12 is reflected in a reflecting mirror 13, and a sample 14 which is installed in the sample installation unit 107 is irradiated with terahertz light 12 by an inclination of 10°. The terahertz light 12 (reflection light 108 (FIG. 1)) which is reflected from the sample 14 by an inclination of 10° is reflected in a reflecting mirror 15, and received by a Deuterium Tri-Glycine Sulfate (DTGS) detector 16 which functions as the reflection light detection unit 109. Meanwhile, if it is possible to irradiate the sample 14 with terahertz light, another crystal may be used instead of the DAST crystal 11. In addition, a light wave of wavelength in a terahertz band oscillated by femtosecond laser may be used.

The optical parametric oscillator 3 using the DAST crystal 11 as described above is disclosed in H. Ito, K. Suizu, T. Yamashita, A. Nawahara and T. Sato, "Random Frequency Accessible Broad Tunable Terahertz-Wave Source Using Phase-Matched 4-Dimethylamino-N-methyl-4-stilbazolium Tosylate Crystal," Japanese Journal of Applied Physics Vol. 46 No. 11(2007) pp. 7321-7324.

Here, it is possible to measure reflectance as follows. First, a reference plate (for example, a gold mirror) which is not shown in the drawing is installed in the sample installation unit 107 instead of the sample 14. Light obtained in such a way that the terahertz light 12 which is irradiation light is reflected in the reference plate is detected by the DTGS detector 16 which functions as the reflection light detection unit 109. A result of the detection is defined as irradiation light intensity.

Subsequently, the reference plate is removed from the sample installation unit 107, and the sample 14 is installed in the sample installation unit 107. Light obtained in such a way that the terahertz light 12 which is irradiation light is reflected in the sample 14 is detected by the DTGS detector 16 which functions as the reflection light detection unit 109. A result of the detection is defined as reflection light intensity.

The reflectance determination unit 111 measures (determines) a value, obtained by dividing the reflection light intensity by the irradiation light intensity, as reflectance.

Meanwhile, in addition to the values which have been described here, another value which is correlated with the reflectance of terahertz light from the conductive thin film may be acquired as the reflectance.

Figure 3:
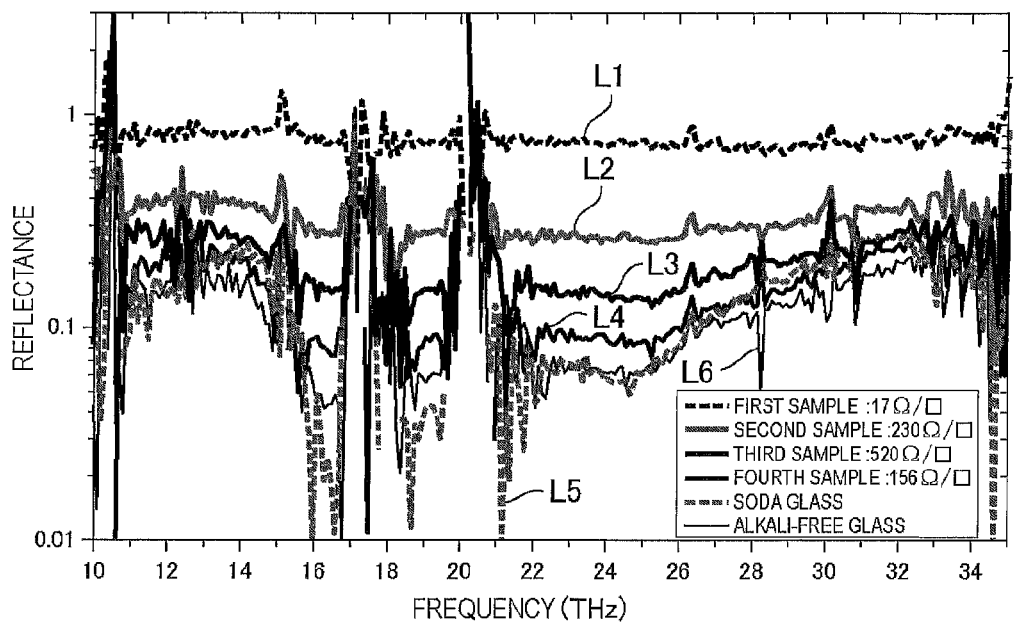
FIG. 3 is a view illustrating the relationship between frequency and reflectance of terahertz light.

FIG. 3 is a view illustrating the relationship between the frequency and reflectance of terahertz light.

A curved line L1 indicates a result of measurement when using a first sample which is obtained in such a way that an Indium Zinc Oxide (IZO) film which functions as a conductive thin film is formed on a soda glass plate which functions as a base substrate by a film thickness of 200 nm.

A curved line L2 indicates a result of measurement when using a second sample which is obtained in such a way that an Indium Tin Oxide (ITO) film which functions as the conductive thin film is formed on an alkali-free glass plate which functions as the base substrate by a film thickness of 100 nm.

A curved line L3 indicates a result of measurement when using a third sample which is obtained in such a way that the ITO film which functions as the conductive thin film is formed on the alkali-free glass plate which functions as the base substrate by a film thickness of 30 nm.

A curved line L4 indicates a result of measurement when using a fourth sample which is obtained in such a way that the ITO film which functions as the conductive thin film is formed on the alkali-free glass plate which functions as the base substrate by a film thickness of 10 nm.

In all of the first to fourth samples, the base substrate has a side of 25 mm and a thickness of 1 mm.

Meanwhile, a curved line L5 indicates a result of measurement when only the soda glass plate which functions as the base substrate is installed in the sample installation unit 107. In addition, a curved line L6 indicates a result of measurement when only the alkali-free glass plate which functions as the base substrate is installed in the sample installation unit 107.

In the first to fourth samples, the surface resistance of each of the conductive thin films is obtained using contact measurement. The surface resistance of a sample 1 is 17Ω/□. The surface resistance of a sample 2 is 230Ω/□. The surface resistance of a sample 3 is 520Ω/□. The surface resistance of a sample 4 is 1560Ω/□.

From a result of FIG. 3, it is understood that there is a tendency for reflectance to drop as the surface resistance is larger.

Here, the reflectance of a background (base substrate) is mixed in the result of the measurement. Therefore, when the reflection components of the thin films are compared, it is necessary to confirm that the reflectance of each base substrate is the same. As an example, with regard to each of the reflectance of the alkali-free glass and the soda glass which function as the base substrates, the same reflectance is shown at 23 THz. This shows that the reflection component of only the conductive thin film can be read at 23 THz regardless of the type of a glass.

Figure 4:
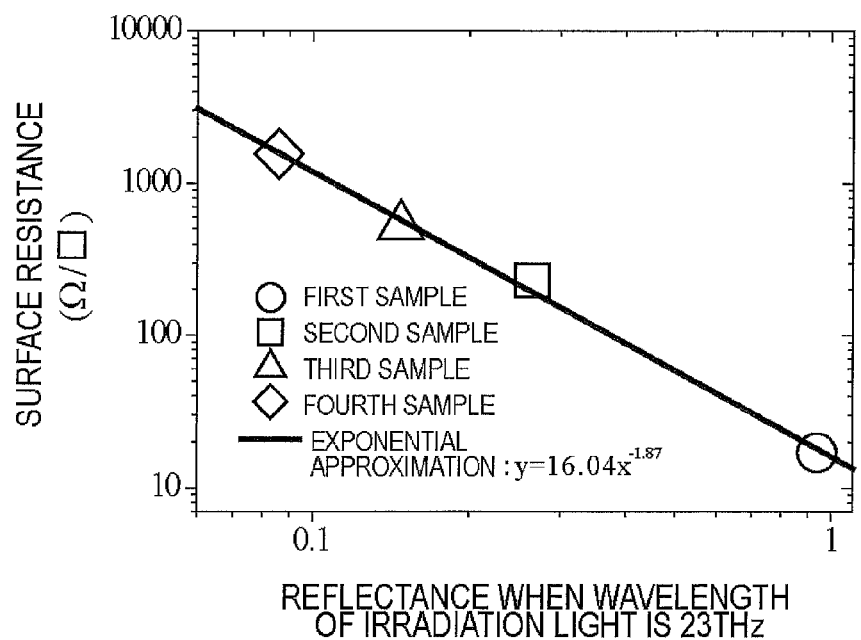
FIG. 4 is a view illustrating the relationship between the reflectance of terahertz light and surface resistance.

FIG. 4 is a view illustrating the relationship between the reflectance and surface resistance when the wavelength of terahertz light which is irradiation light is 23 THz.

From FIG. 4, it can be understood that the surface resistance is expressed using exponential approximation in the following Equation 1.

$$y=16.04x^{-1.87} \quad (1)$$

Therefore, Equation 1 is stored in the storage 101. When the wavelength of terahertz light which is irradiation light is 23 THz, it is possible to calculate the surface resistance as a value of "y" in Equation 1 by substituting reflectance which is determined by the reflectance determination unit 111 for "x" in Equation 1.

Meanwhile, since the reflectance of the soda glass is the same as the reflectance of the alkali-free glass, and, in particular, the reflectance is low at 23 THz, the difference in the reflectance of the thin films can be considerably obtained. In the same manner, the difference can be measured at 25 THz. Even though reflectance is some high in the vicinity of 12 THz and in the vicinity of 12 THz, reflectance can be measured.

In addition, when another glass is used as the base substrate instead of the soda glass or the alkali-free glass, if it is possible to confirm a frequency which is the same as the reflectance of the soda glass or the alkali-free glass, the measurement can be performed using the same method as in the embodiment.

According to the first embodiment as described above, the correlation (Equation 1) between the reflectance of terahertz light from the conductive thin film and the electrical resistance of the conductive thin film is stored in the storage 101 in advance. Further, the reflectance of terahertz light from the conductive thin film is determined, and thus it is possible to determine the electrical resistance of the conductive thin film based on a result of the determination and the correlation. Therefore, it is possible to measure (determine) the electrical resistance of the conductive thin film in a contactless manner.

It is apparent that the present invention is not limited to the above embodiment, and may be modified and changed without departing from the scope and spirit of the invention.

What is claimed is:

1. An electrical resistance measurement apparatus comprising:
    a light irradiation unit that irradiates a conductive thin film with terahertz light;
    a reflection light detection unit that detects reflection light from the conductive thin film; and
    a computer containing a storage that stores a single equation representing correlation between the reflectance of the terahertz light from the conductive thin film and electrical resistance of the conductive thin film,
    the computer further containing a processor that determines reflectance of the terahertz light from the conductive thin film based on a result of detection performed by the reflection light detection unit, and calculates the electrical resistance of the conductive thin film by substituting the reflectance obtained by the determination into the equation,
    wherein the single equation is an exponential approximation equation $y=A \cdot x^B$, where x is the reflectance of the terahertz light from the conductive thin film, y is the electrical resistance of the conductive thin film, and A and B are constants;
    the light irradiation unit radiates the terahertz light having a frequency of 23 THz; and
    the exponential approximation equation is $y=16.04x^{-1.87}$.

2. The electrical resistance measurement apparatus according to claim 1,
    wherein the electrical resistance is surface resistance.

3. The electrical resistance measurement apparatus according to claim 1,
    wherein the conductive thin film is an Indium Tin Oxide (ITO) film.

4. The electrical resistance measurement apparatus according to claim 1,
    wherein the conductive thin film is an Indium Zinc Oxide (IZO) film.

5. An electrical resistance measurement method comprising:
    irradiating a conductive thin film with terahertz light;
    detecting reflection light from the conductive thin film;
    determining reflectance of the terahertz light from the conductive thin film based on a result of detection performed in said step of detecting the reflection light; and
    calculating the electrical resistance of the conductive thin film by substituting the reflectance obtained in said step of determining the reflectance into a single equation representing correlation between the reflectance of the terahertz light from the conductive thin film and the electrical resistance of the conductive thin film,
    wherein the single equation is an exponential approximation equation $y=A \cdot x^B$, where x is the reflectance of the terahertz light from the conductive thin film, y is the electrical resistance of the conductive thin film, and A and B are constants;
    a frequency of the terahertz light is 23 THz; and
    the exponential approximation equation is $y=16.04x^{-1.87}$.

6. The electrical resistance measurement method according to claim 5,
    wherein the electrical resistance is surface resistance.

7. The electrical resistance measurement method according to claim 5,
    wherein the conductive thin film is an Indium Tin Oxide (ITO) film.

8. The electrical resistance measurement method according to claim 5,
    wherein the conductive thin film is an Indium Zinc Oxide (IZO) film.

* * * * *